US005517571A

United States Patent [19]

Saruta et al.

[11] Patent Number: 5,517,571

[45] Date of Patent: May 14, 1996

[54] ACTIVE NOISE ATTENUATING DEVICE OF THE ADAPTIVE CONTROL TYPE

[75] Inventors: Susumu Saruta, Hirakata; Yasuyuki Sekiguchi, Takatsuki, both of Japan

[73] Assignee: Kabushiki Kaisha Toshiba, Kawasaki, Japan

[21] Appl. No.: 214,325

[22] Filed: Mar. 17, 1994

[30] Foreign Application Priority Data

Mar. 17, 1993 [JP] Japan .................................... 5-056744

[51] Int. Cl.[6] ............................ A61F 11/06; H03B 29/00; H04B 15/00

[52] U.S. Cl. ................................................ 381/71; 381/94

[58] Field of Search .............................. 381/71, 73.1, 94, 381/93, 13; 364/724.2, 724.1, 724.19; 379/410, 411

[56] References Cited

U.S. PATENT DOCUMENTS

| | | | |
|---|---|---|---|
| 4,596,033 | 6/1986 | Swinbanks | 381/71 |
| 5,018,202 | 5/1991 | Takahash et al. | 381/71 |
| 5,192,918 | 3/1993 | Sugiyama | 381/71 |
| 5,278,913 | 1/1994 | Dolfosse et al. | 381/71 |
| 5,293,578 | 3/1994 | Nagami et al. | 381/71 |
| 5,319,715 | 6/1994 | Nagami et al. | 381/71 |
| 5,404,409 | 4/1995 | Nagami et al. | 381/71 |

*Primary Examiner*—Forester W. Isen
*Assistant Examiner*—Xu Mei
*Attorney, Agent, or Firm*—Cushman Darby & Cushman

[57] ABSTRACT

An active noise attenuating device includes a first microphone located in a propagation path of noise, a loud speaker located downstream from the first microphone, a second microphone located downstream from the loud speaker for receiving sound, and an operational unit for executing an operation on the basis of a detection signal from the first microphone to generate a control signal supplied to the loud speaker so that a sound interfering with the noise is produced. An operational factor of the operational unit is controlled by an adaptive controller on the basis of the detection signal from the second microphone so that an amount of noise attenuated by the sound produced from the loud speaker is rendered maximum. A transfer characteristic of a transfer path between the loud speaker and the second microphone is identified on the basis of the detection signals generated by the second microphone when a sound represented by a periodical identifying signal is produced in a plurality of periods. An operational factor of the adaptive controller is adjusted by an adaptive control identifying unit on the basis of the identified transfer characteristic.

9 Claims, 6 Drawing Sheets

ACTIVE NOISE ATTENUATING DEVICE OF THE ADAPTIVE CONTROL TYPE

BACKGROUND OF THE INVENTION

1. Field of the Invention

This invention relates to an active noise attenuating device provided in a propagation path of noise for producing a sound having the same amplitude as that of the noise and a phase opposite to the noise, to cause a sound interference between the noise and the produced sound, thereby attenuating the noise.

2. Description of the Prior Art

An active noise attenuating device has recently been proposed for attenuating noise produced by an air conditioner and propagating along a draft duct thereof. The active noise attenuating device produces a sound having the same amplitude as that of the noise and a phase opposite to the noise to cause a sound interference in the draft duct, thereby actively attenuating the noise and reducing an amount of noise leaking out of the draft duct.

An active noise attenuating technique applied to the above-described device employs applied electronic techniques and particularly, an acoustic data processing circuit arrangement and acoustic interference. In this active noise attenuating technique, basically, a sound receiver such as a microphone is provided in the draft duct to detect the sound from a noise source, thereby converting the detected sound to a corresponding electrical signal. The electrical signal is processed into a signal by an operation unit. The signal is supplied to a control sound producer such as a loud speaker so that it produces an artificial sound having the same amplitude as of the noise and the phase opposite to the noise, at a control point and so that the artificial sound interferes with the noise at the control point. Consequently, an attenuation efficiency can be expected to amount to 10 dB or more in a low frequency band in the above-described device. Moreover, no pressure loss occurs in the above noise attenuating device. For example, when a concert hall is equipped with the above-described active noise attenuating device, noise produced from the draft ducts can be attenuated such that a better space can be provided for appreciation of music.

In employment of the active noise control in practice, characteristic variations due to aged deterioration of parts composing the signal system and due to an ambient temperature need to be coped with. For this purpose, an operational factor or acoustic transfer function of the operation unit is adjusted in accordance with variations in the noise attenuating performance of the device. More specifically, a monitoring sound receiver such as a microphone is provided for monitoring the noise attenuating effect of the control sound producer. Adaptive control means is also provided for controlling the operation unit. When the monitorial result is out of a predetermined allowable range, the adaptive control means changes the operational factor of the operation unit so that the monitorial result is within the allowable range. Consequently, the noise attenuation performance in the active noise control is maintained at its optimum in accordance with the characteristic variations. This control manner is referred to as "adaptive control."

FIGS. 7 and 8 illustrate an example of the conventional active noise attenuating device as described above. Referring to FIG. 7, a duct 1 has a closed end and an open end. A noise source 2 is disposed at the side of the closed end in the duct 1. An active noise attenuating device 3 is provided for preventing noise produced from the noise source 2 from leaking out of an opening la of the duct 1. A sound source microphone 4 for detecting noise, a loud speaker 5 producing an interference sound and a monitoring microphone 6 as will be described later are disposed at respective points S, A and O along a noise propagation path in the duct 1. The noise from the noise source 2 is detected by the microphone 4 at point S, and the microphone 4 generates a detection signal indicative of the detected noise. The detection signal is supplied to a control section 7 in which the detection signal is processed into a control sound such that the sound pressure becomes zero by acoustic interference at point O in the vicinity of the opening 1*a* when it is produced from the loud speaker 5. When the control sound is produced from the loud speaker 5 to be directed to the opening la of the duct 1, the acoustic interference is caused between the noise and the control sound such that a so-called acoustic wall is formed. The noise is prevented by the acoustic wall from leaking out of the opening 1*a*. The monitoring microphone 6 measures an amount of attenuated noise at point O and generates a detection signal indicative of the measured amount of attenuated noise. The detection signal is supplied to the control section 7. The control section 7 previously measures the acoustic transfer characteristic of the duct 1 and the transfer characteristics of the sound source microphone 4 and the loud speaker 5 in order that a signal for producing the control sound is generated. Based on the results of the measurement, the characteristic of a filter for processing the detection signal from the sound source microphone 4 is obtained.

A method of obtaining the filter characteristic will be described. In the following description, reference symbol $G_{AO}$ designates the acoustic transfer characteristic of a transfer path between point A indicative of the location of the loud speaker 5 and point O indicative of the location of the monitoring microphone 6. Reference symbol $G_{SO}$ designates the acoustic transfer characteristic of a transfer path between point S indicative of the location of the sound source microphone 4 and point O. Reference symbol $G_{SA}$ designates the acoustic transfer characteristic of a section between point S where the noise is received by the microphone 4 and point A where the control sound obtained by processing the detection signal indicative of the received sound is produced. First, a random noise such as a white noise is produced from the loud speaker 5 so that the acoustic transfer characteristic $G_{AO}$ is measured. The acoustic transfer characteristic $G_{SO}$ is then measured in the condition that the random noise is being produced from the loud speaker 5. Then, the acoustic transfer characteristic $G_{SO}$ can be shown by the following expression:

$$G_{SO}=G_{SA}\cdot G_{AO}. \tag{1}$$

Consequently, the transfer characteristic G of a filter of the control section 7 needs to have an opposite phase with the acoustic transfer characteristic $G_{SA}$. From the equation (1), the transfer characteristic G of the filter is obtained as follows:

$$G=-G_{SA}=-G_{SO}/G_{AO}. \tag{2}$$

Accordingly, the noise can be attenuated by the control sound produced from the loud speaker 5 at point O indicative of the location of the monitoring microphone 6 when the transfer characteristic G of the filter is set for a value shown by the equation (2).

In order that a sufficient noise attenuating effect is always achieved, the control sound needs to be automatically adjusted in consideration of the variations of the acoustic transfer characteristic in the duct 1 due to aged deterioration of the sound source microphone 4 and the loud speaker 5 and the changes in the ambient temperature and the like. For this purpose, the prior art has proposed active noise attenuation system of the adaptive control type as disclosed in Japanese Unexamined Patent Application Publication No. 61-296392. In the disclosed system, sound unattenuated by the control sound is detected by a monitoring microphone disposed at point O or an aural null. A control section is controlled in a feedback manner so that an amount of the sound detected by the monitoring microphone is rendered the minimum, whereby the noise attenuation effect is maintained at a high level.

FIG. 8 illustrates the arrangement of the control section in the noise attenuation system of the adaptive control type as described above. The detection signal from the sound source microphone 4 is supplied both to a noise attenuating filter 8 and to another filter 9 which is set for the transfer characteristic $G_{AO}$ of the transfer path between the loud speaker 5 and the monitoring microphone 6. An adaptive filter 10 is supplied with a signal from the filter 9 and a detection signal from the monitoring microphone 6 via an operation unit 11. In this system, too, the acoustic transfer characteristic $G_{AO}$ of the transfer path between the loud speaker 5 and the monitoring microphone 6 is previously obtained in the same manner as described above. A detection signal y indicative of the sound detected at point O is shown by the following expression:

$$y=G_{SO}\cdot x \tag{3}$$

where x is a detection signal indicative of the noise reaching the sound source microphone 4. A signal −y having a phase opposite to the detection signal y needs to be superimposed on the signal y at point O in order that the signal y is rendered zero. The signal −y is obtained from the following equation:

$$-y=G_{AO}\cdot a \tag{4}$$

where a is a signal indicative of the sound produced from the loud speaker 5. Using G for the characteristic of the noise attenuating filter 8, $$a=G\cdot x=-G_{SO}/G_{AO}\cdot x \tag{5}$$

and $$y=(-G)\cdot G_{AO}\cdot x. \tag{6}$$

Accordingly, −G is obtained from the detection signal y of the monitoring microphone 6 and the signal $G_{AO}\cdot x$ obtained by processing the detection signal x of the sound source microphone 4 by the filter 9 with the acoustic transfer characteristic $G_{AO}$, by way of identification by the adaptive filter 10 and the operation unit 11. Then, the characteristic of the filter 8 is obtained by way of sign change. When a digital filter is used for the processing, the characteristic is obtained in the form of a filter factor. Accordingly, the sign change can be obtained by subtracting each tap factor value from zero.

When the spatial acoustic transfer characteristic $G_{SO}$ is shifted to $G_{SO}'$ by environmental changes or the like, the optimum value $G_{new}$ of the characteristic of the noise attenuating filter 8 is shifted by ΔG relative to the present noise attenuating filter characteristic $G_{old}$. The optimum value $G_{new}$ is shown by the following expression:

$$G_{new}=G_{old}-\Delta G. \tag{7}$$

In this case, the detection signal y' indicative of the unattenuated noise detected at point O is shown by the following equation:

$$y'=x\cdot G\cdot G_{AO}+x\cdot G_{SO}'. \tag{8}$$

Accordingly, the relationship at the time of an optimum noise attenuation is shown by the following equation:

$$x(G-\Delta G)\cdot G_{AO}+x\cdot G_{SO}'=0. \tag{9}$$

Eliminating $G_{SO}'$ from equations (8) and (9), we have:

$$y'=x\cdot G\cdot G_{AO}-x\cdot(G-\Delta G)\cdot G_{AO}=(x\cdot G_{AO})\cdot\Delta G. \tag{10}$$

Accordingly, the deviational component ΔG of the filter characteristic G is obtained from the detection signal y' from the monitoring microphone 6 and the signal $G_{AO}\cdot x$ obtained by processing the sound source signal x by the filter 9 having the filter characteristic $G_{AO}$, by way of identification by the adaptive filter 10 in the same manner as in the equation (6). Consequently, a new optimum noise attenuation filter characteristic of the filter 8 can be obtained from the equation (7). When the equation (6) is compared with those (7) and (10), the acoustic transfer characteristic G of the noise attenuation filter 8 to be initially obtained corresponds to the value of the equation (7) where 0 is substituted for $G_{old}$. Thus, an optimum noise attenuation can be obtained when the adaptive processing and the factor renewal processing represented respectively by the equations (10) and (7) where 0 is substituted for the initial value of the characteristic of the filter 8 are repeated. Actually, however, the factor renewal is performed by multiplying ΔG by a feedback gain parameter μ rather than using the equation (7) as follows:

$$G_{new}=G_{old}-\mu\Delta G. \tag{11}$$

In the case where the feedback gain parameter μ is employed, the convergence speed and the stability can be improved or adjusted advantageously. However, the acoustic transfer characteristic $G_{SO}$ of the transfer path between the loud speaker 5 and the sound source microphone 4 and the acoustic transfer characteristic $G_{AO}$ of the transfer path between the loud speaker 5 and the monitoring microphone 6 need to be measured and identified prior to initiation of the noise attenuating operation. Accordingly, when the noise attenuating control is started in the condition that the noise is being produced from the noise source 2, an accurate identification cannot be performed, which provides insufficient noise attenuating effect.

In view of the above-described problem, the active noise attenuating device is conventionally started first and the identification of the acoustic transfer characteristics is then performed. Thereafter the air conditioner or the like which is a noise source 2 is started. Accordingly, since the air conditioner cannot be driven at once when connected to a power source, the air conditioning operation cannot be performed promptly. Furthermore, the acoustic transfer characteristic $G_{AO}$ varies out of the range of the adaptive control by the adaptive filter 10 when the changes in the temperature, the aged deterioration or the like changes the condition of the duct 1 during the noise attenuating operation. Since the noise attenuating effect by the active noise control is lowered in such a case, the acoustic transfer characteristic need to be reidentified. However, the acoustic transfer characteristic can be identified only when the noise is not produced from the noise source 2. Accordingly, the air conditioner needs to be once turned off for the purpose of execution of the identification of the acoustic transfer characteristic. Consequently, the efficiency in operation of the air conditioner is lowered.

In view of the foregoing, the following countermeasure has been proposed. An identifying sound louder than the noise produced from the noise source 2 is produced from the loud speaker 5 so that the signal-to-noise (S/N) ratio of the identifying sound relative to the noise is increased, whereby the acoustic transfer characteristic can be identified even during drive of the air conditioner. However, the sound louder than the noise is produced from the loud speaker 5 provided for attenuating the noise, during the processing of the identification of the acoustic transfer characteristic. Thus, the active noise attenuating device cannot perform its function during this processing and moreover, the device itself becomes a noise source. Consequently, the above-described countermeasure is impractical.

SUMMARY OF THE INVENTION

Therefore, an object of the present invention is to provide an active noise attenuating device wherein the acoustic transfer characteristic can be accurately identified without interruption of the noise attenuation even while the noise is propagating along the propagation path.

The present invention provides an active noise attenuating device of an adaptive control type comprising a first microphone provided in a propagation path of noise for receiving the same, thereby generating a detection signal indicative of the received noise, a loud speaker provided downstream from the first microphone along the noise propagation path, and a second microphone provided downstream from the loud speaker along the noise propagation path for receiving sound, thereby generating a detection signal indicative of the received sound. Operation means is provided for executing an operation on the basis of the detection signal from the first microphone, thereby generating a control signal supplied to the loud speaker so that a sound interfering with the noise is produced therefrom, whereby the noise is attenuated. Adaptive control means is connected to the first and second microphones for adjusting an operational factor of the operation means on the basis of the detection signals supplied thereto from the first and second microphones, respectively so that an amount of noise attenuated by the sound produced from the loud speaker is rendered maximum.

Filter means is provided an input line through which the detection signal of the first microphone is supplied to the adaptive control means. The filter means processes the input detection signal by means of predetermined transfer characteristic. A signal generator is provided for delivering to the loud speaker an identifying signal generated so as to be repeated in predetermined periods and having frequency components ranging in a frequency band of the noise to be attenuated. First synchronous adding means is provided for adding the detection signals generated by the second microphone sychchronous with the period of the identifying signal in a number of periods, said detection signals being generated by the second microphone when the sound represented by the identifying signal and produced from the loud speaker is received by the same. The first synchronous adding means obtains an average value of the added detection signals and generates an output signal indicative of the obtained average value. Adaptive control indentification control means is provided for identifying a transfer characteristic of a transfer path between the loud speaker an the second microphone on the basis of the output signal from the first synchronous adding means and the identifying signal and for adjusting a filtering characteristic of the filter means so that the filtering characteristic remains identical with the identified transfer characteristic.

The sound represented by the identifying signal is produced from the loud speaker and received by the second microphone, which generates the detection signal. Based on the output signal from the first synchronous adding means and the identifying signal, the adaptive control identification control means identifies the transfer characteristic of the transfer path between the loud speaker and the second microphone, prior to initiation of the active noise control. The adaptive control identification control means further adjusts the filtering characteristic of the filter means so that the filtering characteristic remains identical with the identified transfer characteristic. Since the identifying signal has periodicity, data in a phase from the start of each period always takes the same value. Accordingly, when the transfer path of the signal including the propagation path of the noise is considered steady, the same response can be obtained in each period of the sound represented by the identifying signal. When the data are added in synchronism with the period of the identifying signal over a plurality of periods and the added data are averaged, the component of the detection signal takes a substantially invariable value. On the other hand, in the case where a random signal or a signal having periodicity differing from that of the identifying signal is superimposed upon the identifying signal, noise signals other than the identifying signal are damped as the data are added and averaged over the plurality of periods. For example, when the data of the identifying signals are added and averaged over n periods, amplitude components of the superimposed noise signals can be damped so as to be proportional to the reciprocal of the square root of n. More specifically, the amplitude components of the noise signals are damped to a half when the data are added and averaged four times, one fifth when twenty-five times, and one tenth when one hundred times. When the damping (signal-to-noise (S/N) ratio) is shown in decibel (dB), these are 6 dB, 14 dB and 20 dB respectively. Accordingly, the noise components other than the identifying signal can be damped and the detection signal with high S/N ratio can be obtained when the detection signals indicative of the identifying signals over a plurality of periods are employed. Consequently, since the transfer characteristic of the transfer path between the loud speaker and the second microphone can be accurately identified, the accuracy of the adaptive control by the adaptive control means can be improved and the amount of attenuated noise can be rendered maximum.

In the above-described active noise attenuating device, the state that the operation means and the adaptive control means are connected to the first and second microphones and the loud speaker and the state that the adaptive control identification means is connected to the first and second microphones and the loud speaker may be simultaneously set. The noise attenuating operation and the identifying processing can be simultaneously performed when the above-described two states are simultaneously set. The transfer characteristic can be accurately identified even when the noise component is large relative to the identifying signal, as described above. Accordingly, the transfer characteristic can be accurately identified without hindrance by the noise even while the noise is propagating from the noise source along the propagation path. Furthermore, even when the acoustic transfer characteristic is varied by the aged deterioration of the propagation path or temperature changes, the transfer characteristic can be reliably identified without interruption of the operation of the noise source and the active noise control can be performed with the noise attenuating effect at a high level. This means that the level of the identifying signal in the identifying processing can be set to a small value relative to the control sound of the noise attenuation control. Thus, the noise attenuation control can be performed without any hindrance.

The above-described active noise attenuating device may further comprise cancel means provided with a transfer characteristic same as that of a transfer path between the loud speaker and the first microphone for subtracting a cancel signal from the detection signal generated by the first microphone, the cancel signal being obtained by filtering the control signal generated by the operation means, second synchronous adding means for adding the detection signals generated by the first microphone synchronous with the period of the identifying signal in a number of periods, said detection signals being generated by the first microphone when the sound represented by the identifying signal and produced from the loud speaker is received by the first microphone, the second synchronous adding means obtaining an average value of the added detection signals and generating an output signal indicative of the obtained average value, and canceling identification control means for identifying a transfer characteristic of a transfer path between the loud speaker and the first microphone on the basis of the output signal of the second synchronous adding means and the identifying signal and for adjusting the transfer characteristic of the cancel means on the basis of the identified transfer characteristic.

BRIEF DESCRIPTION OF THE DRAWINGS

Other objects, features and advantages of the present invention will become clear upon reviewing the following description of preferred embodiments thereof, made with reference to the accompanying drawings, in which.

DESCRIPTION OF THE PREFERRED EMBODIMENTS

A first embodiment of the present invention will be described with reference to FIGS. 1 to 4 of the accompanying drawings. In the first embodiment, the active noise attenuating device of the invention is applied to a draft duct of an air conditioning system.

Figure 1:
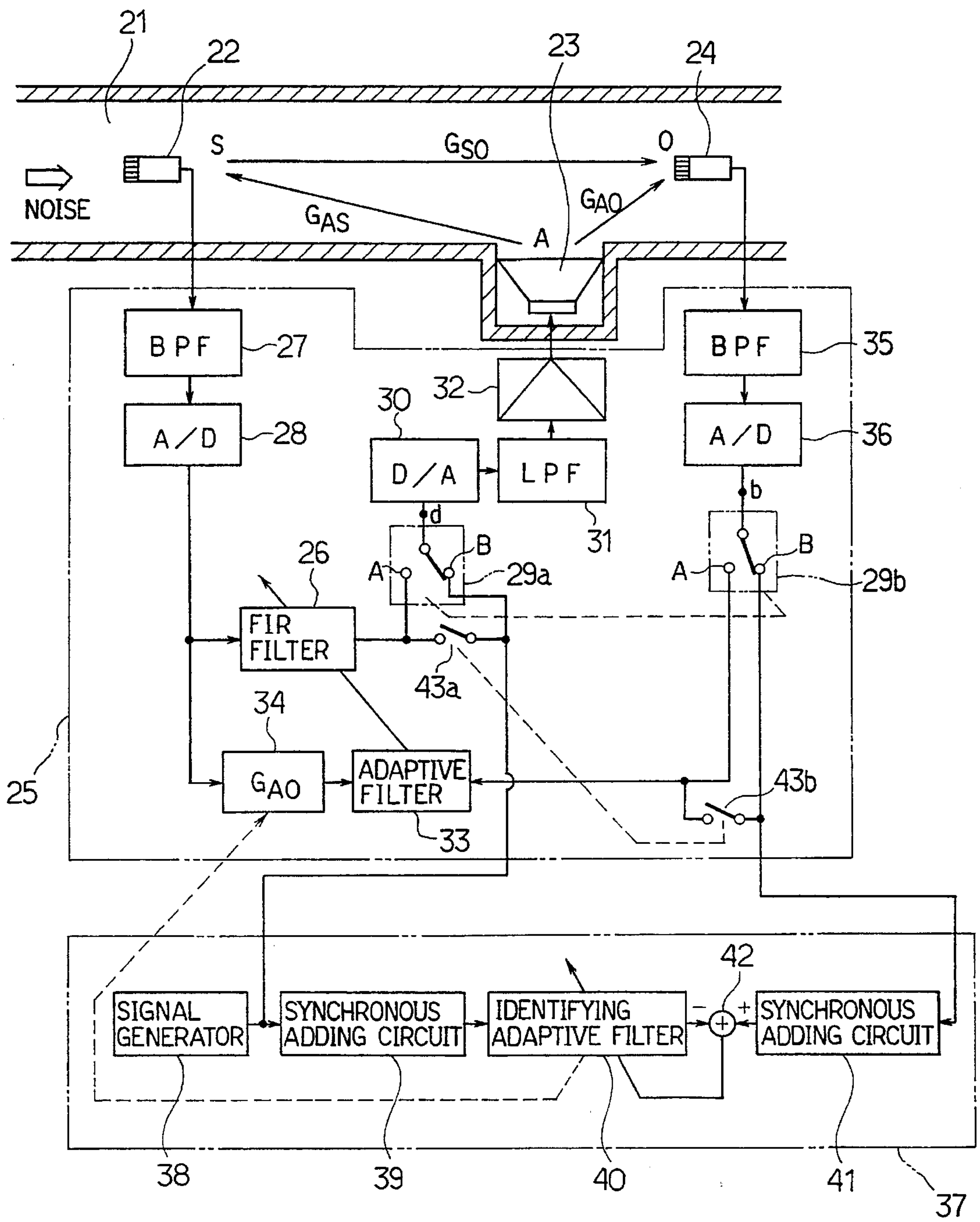
FIG. 1 is a block diagram of a first embodiment of an active noise attenuating device in accordance with the present invention.

Referring to FIG. 1, the air conditioning system (not shown) is provided at the left hand of a draft duct 21. Conditioned air from the air conditioning system is supplied through the duct 21 to the right, as viewed in FIG. 1. The draft duct 21 serves as a propagation path of noise produced from the air conditioning system serving as a noise source as well as a flow path of the air. The duct 21 has a generally 50 centimeters square section, for example. A first microphone or sound source microphone 21 is disposed in the draft duct 21 for detecting the noise propagating in it, thereby generating a detection signal indicative of the detected noise. A loud speaker 23 is disposed downstream from the microphone 22 or at a predetermined position in the right of it in the duct 21, as viewed in FIG. 1. The loud speaker 23 produces an interference sound interfering with the noise, as will be described later. A second microphone or monitoring microphone 24 is disposed in the vicinity of the loud speaker 23 at the right hand thereof. The monitoring microphone 24 detects the interference sound produced from the loud speaker 23 for the purpose of evaluating an effect of noise attenuation, thereby generating a detection signal indicative of the detected interference sound. The detection signals generated by the microphones 22 and 24 are supplied to a control circuit 25, which generates a control signal for production of the interference sound on the basis of the detection signals supplied thereto. The control signal is supplied to the loud speaker 23. More specifically, the detection signal generated by the microphone 22 is supplied via a band path filter (BPF) 27 and an analog-to-digital (A/D) converter 28 to an input section of a finite impulse response (FIR) filter 26 composing operation means. The FIR filter 26 having a transfer characteristic G performs an operation to process the input signal by filtering to thereby generate the control signal, as will be described later. The control signal is supplied to the loud speaker 23 via a change-over switch 29*a*, a digital-to-analog (D/A) converter 30, a low pass filter (LPF) 31 and an amplifier 32 in turn. The BPF 27 is adapted to allow a frequency component ranging between 50 and 800 Hz (upper limit) to pass therethrough with respect to the detection signal supplied thereto from the microphone 22. The A/D converter 28 samples the input signal at a sampling frequency f (2 kHz, for example) twice as high as the upper limit (800 Hz) of the pass frequency band of BPF 27 or above, thereby converting the input signal to a digital signal. The sampling frequency f is set to satisfy a sampling theorem for the sound to be attenuated whose frequency ranges in a frequency band from 50 to 350 Hz. LPF 31 is provided for cutting off an alias component of higher harmonics contained in an analog signal obtained by the D/A converter 30. An adaptive filter 33 is provided for adjusting an operational factor of the FIR filter 26. The adaptive filter 33 is supplied with the detection signal from the A/D converter 28 via a digital filter 34 having a transfer characteristic $G_{AO}$. Furthermore, the detection signal generated by the monitoring microphone 24 is supplied to the adaptive filter 33 via BPF 35, an A/D converter 36 and a change-over switch 29*b*. BPF 35 has the same band-pass characteristic as of BPF 27 and is set for the same sampling frequency as set therein. The A/D converter 36 also has the same band-pass characteristic as of the A/D converter 28 and is set for the same sampling frequency as set therein. A filtration characteristic $G_{AO}$ of the digital filter 34 corresponds to an acoustic transfer characteristic of a transfer path between point "a" representative of an output portion of the FIR filter 26 and point "b" representative of an output terminal of the A/D converter 36 via the D/A converter 30, LPF 31, the amplifier 32, the loud speaker 23, the draft duct 21, the monitoring microphone 24, BPF 35 and the A/D converter 36. The filter characteristic $G_{AO}$ of the digital filter 34 is set with the acoustic transfer characteristic $G_{AO}$ identified by an identification control section 37, as will be described later. Each of the changeover switches 29*a*, 29*b* serving as switching means is switched from a terminal A to a terminal B when an identifying processing is performed, as will be described later.

A signal generator 38 in the identification control section 37 generates as an identifying signal an M-sequence pseudorandom noise signal, for example. The M-sequence pseudorandom noise signal contains a frequency signal covering the frequency band of the noise to be attenuated and is repeated in predetermined periods. The M-sequence pseudorandom noise signal is generated by a nine-stage shift register as a digital signal having a unit length of "511." The period of the digital signal is equal to the width of 511 pulses. The M-sequence pseudorandom noise signal generated by the signal generator 38 is supplied to the loud speaker 23 via the terminal B of the change-over switch 29*a*, the D/A converter 30, LPF 31 and the amplifier 32 in turn. Upon receipt of the M-sequence pseudorandom noise signal, the loud speaker 23 produces an identifying sound directed into the draft duct 21. The M-sequence pseudorandom noise signal generated by the signal generator 38 is also supplied via an identification adding circuit 39 to an identifying adaptive filter 40 serving as identification control means. The detection signal generated by the monitoring microphone 24 upon receipt of the identifying sound is supplied to a synchronous adding circuit 41 serving as synchronous adding means via BPF 35, the A/D converter 36 and the change-over switch 29*b*. The synchronous adding circuit 41 adds the detection signals supplied thereto from the monitoring microphone 24 in synchronism with the period of the identifying signal and further obtains an average value of the added signals. An output signal indicative of the average value is supplied as a reference signal to an operation unit 42. The operation unit 42 has a subtraction input terminal to which an output signal of the identifying adaptive filter 40 is supplied. An output signal of the operation unit 42 is supplied as an error signal to the identifying adaptive filter 40. The identifying adaptive filter 40 identifies a transfer characteristic of a transfer path between output terminal side point "a" of the FIR filter 26 and point "b" of the input terminal of the adaptive filter 33, that is, the acoustic transfer characteristic $G_{AO}$ of the transfer path between the output terminal of the FIR filter 26 and the change-over switch 29*b* via the change-over switch 29*a*, the D/A converter 30, LPF 31, the amplifier 32, the loud speaker 23, the draft duct 21, the monitoring microphone 24, BPF 35 and the A/D converter 36. The acoustic transfer characteristic identified by the identifying adaptive filter 40 is set as a filter characteristic of the digital filter 34. Switches 43*a* and 43*b* each serving as simultaneous setting means switch the connection between the terminals A and B of the change-over switches 29*a*, 29*b* respectively.

Figure 2:
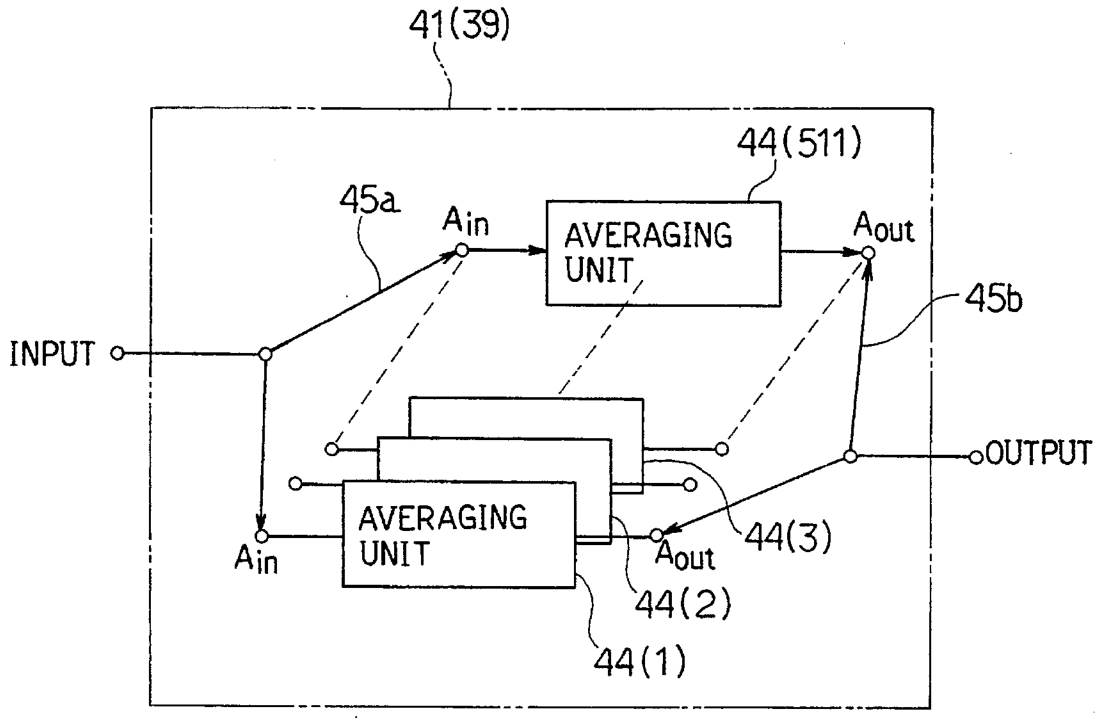
FIG. 2 is a block diagram of a synchronous adding circuit employed in the active noise attenuating device.
Figure 3:
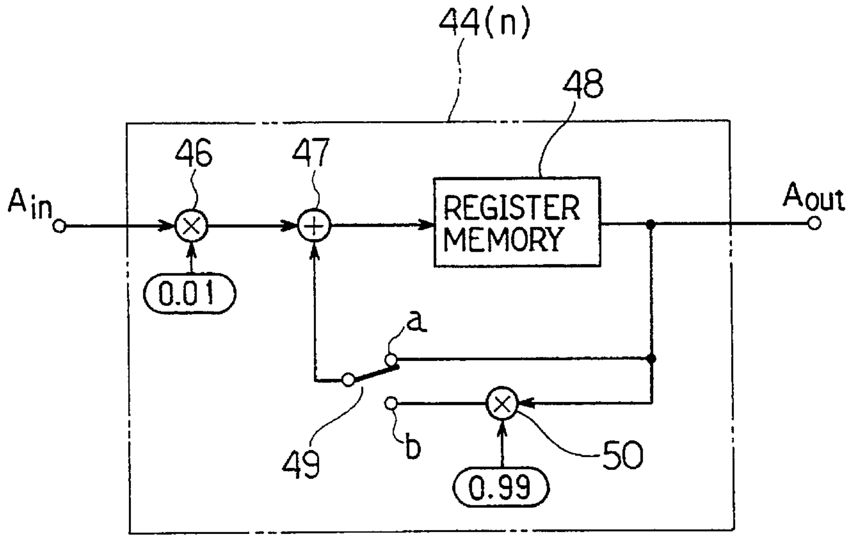
FIG. 3 is a block diagram of averaging units employed in the active noise attenuating device.

FIG. 2 illustrates an arrangement of the synchronous adding circuit 41. The other synchronous adding circuit 39 also has the same arrangement as illustrated in FIG. 2. The synchronous adding circuit 41 is composed of 511 averaging units 44 (n) where n=1, 2, . . . , 511. The number of the averaging units 44 corresponds to the unit length "511" of the pseudorandom noise signal. Data of the pseudorandom noise signal in one period is supplied to each averaging unit 44, which averages the data. These averaging units 44 are switched by switches 45*a* and 45*b* in synchronism with each data. FIG. 3 illustrates an arrangement of each averaging unit 44. Each averaging unit 44 has an input terminal $A_{in}$ connected to an output terminal $A_{out}$ via a multiplier 46, an adder 47 and a register memory 48. The multiplier 46 multiplies an input signal by a constant 0.01 and outputs the result of the multiplication. The register memory 48 memorizes a signal supplied thereto via the adder 47 and outputs the signal. A change-over switch 49 is provided for feeding back the output signal of the register memory 48 thereto. A contact a of the change-over switch 49 is closed so that the output signal of the register memory 48 as it is is supplied to the adder 47, until the sampling is performed at one hundred times, for example. When the sampling is performed at one hundred and one times or more, a contact b of the change-over switch 49 is closed so that the output signal of the register memory 48 is multiplied by the constant 0.99 at a multiplier 50 and the result of the multiplication is supplied to the adder 47.

The operation of the active noise attenuating device will now be described. First, the active noise control operation and the adaptive control operation will be described. The identifying operation by the identification control section will then be described. A. Operation of active noise control and adaptive control:

The frequency band of the noise to be attenuated regarding the draft duct 21 will be first described. The draft duct 21 is formed to have a 50 centimeters square section, as described above. In view of its geometrical dimensions, an upper limit acoustic frequency propagating as a plane wave in the duct 21 is about 350 Hz. Accordingly, sound whose frequency is above 350 Hz cannot become a plane wave and decays with propagation. On the other hand, a lower limit of the frequency of the sound the loud speaker 23 can reproduce is about 50 Hz. Consequently, the frequency band of the noise to be attenuated is set to a range between 50 and 350 Hz.

In the active noise control, the FIR filter 26 having the filter characteristic G performs an operation on the basis of the detection signal from the sound source microphone 22 in the following manner. In this case, the terminal A is closed in each of the change-over switches 29*a*, 29*b*. Equation (1), $G_{SO}=G_{SA}\cdot G_{AO}$, holds where $G_{SO}$ is a transfer characteristic of a transfer path between point S indicative of the location of the sound source microphone 22 and point O indicative of the location of the monitoring microphone 24, $G_{SA}$ a transfer characteristic of a transfer path between point S and point A indicative of the location of the loud speaker 23, $G_{AO}$ a transfer characteristic of a transfer path between points A and O. Accordingly, the filter characteristic G of the FIR filter 26 should be 180 degrees out of phase relative to the acoustic transfer characteristic $G_{SA}$. The filter characteristic G is set to be shown by equation (2), $G=-G_{SA}$, that is, $G=-G_{SO}/G_{AO}$.

The noise produced by the noise source propagates along the duct 21. The noise is detected at point S by the sound source microphone 22, which generates the detection signal indicative of the detected noise. The detection signal is supplied to BPF 27, which cuts off low and high frequency components of the detection signal out of the frequency band of the noise to be attenuated. The signal generated by BPF 27 is sampled at a sampling frequency f (2 kHz, for example) by the A/D converter 28 to be thereby converted to a digital signal. The digital signal is then supplied to the FIR filter 26 having the filter characteristic G performs the operation to process the input digital signal, thereby generating a control signal for production of the interference sound. The control signal is supplied via the change-over switch 29*a* to the D/A converter 30, which converts it to a corresponding analog signal. The analog signal is supplied to LPF 31. The alias component of the higher harmonics contained in the analog signal generated by the D/A converter 30 is cut off by LPF 31. The analog signal processed by LPF 31 is supplied via the amplifier 32 to the loud speaker 23, which produces the control sound corresponding to the supplied signal. The control sound produced from the loud speaker 23 has, at point O indicative of the location of the monitoring microphone 24, the same amplitude as that of the noise having propagated through the duct 21 and a phase opposite to that of the noise or is out of phase substantially by 180 degrees with the noise. Consequently, the control sound interferes with the noise such that the acoustic wall is provided in the duct 21. Propagation of the noise downstream from point O can be prevented by the acoustic wall. The noise reduction of 10 dB or more can be achieved in the above-described objective frequency band in the draft duct 21.

The adaptive control will now be described. In the adaptive control, the operational factor of the FIR filter 26 is adjusted so that the above-described active noise attenuation control is performed in its optimum mode. The sound detected by the monitoring microphone 24 would theoretically approximate to zero while the noise attenuation control is being performed in the duct 21 on the basis of the control signal generated by the FIR filter 26. Actually, however, the temperature and the air flow speed vary depending upon the control state of the air conditioning system. The acoustic transfer characteristic in the duct 21 varies accordingly such that a theoretical amount of attenuated noise cannot be achieved. The adaptive filter 33 is provided for changing the operational factor of the FIR filter 26 in order that the amount of attenuated noise is prevented from being reduced with variations in the acoustic transfer characteristic in the duct 21 during the active noise control.

The monitoring microphone 24 detects the sound having reached point O in the duct 21, thereby generating the detection signal indicative of the detected sound. The detection signal is supplied to the adaptive filter 33 via BPF 35, the A/D converter 36 and the switching circuit **29*b*. On the other hand, a digital signal filtered by the digital filter 34 having the filter characteristic $G_{AO}$ is supplied to the adaptive filter 33. More specifically, the control signal generated by the FIR filter 26 is filtered via the control section between points "a" and "b," which control section has the acoustic transfer characteristic $G_{AO}$. The filtered signal is supplied to the adaptive filter 33. Furthermore, the digital signal supplied from the A/D converter 28 to the FIR filter 26 is filtered by the digital filter 34 also having the same filter characteristic $G_{AO}$, thereby being supplied to the adaptive filter 34. Based on these two input signals, the adaptive filter 33 adjusts the operational factor of the FIR filter 26 using a well known least-mean-square (LMS) algorithm. The filter characteristic $G_{AO}$ of the digital filter 34 is set therein on the basis of data obtained as the result of identification of the acoustic transfer characteristic $G_{AO}$ by the identification control section 37 when the active noise attenuating device is started up, as will be described later. Subsequently, the identification processing is performed at suitable times so that the filter characteristic $G_{AO}$ according to the accurate acoustic transfer characteristic $G_{AO}$ is usually set. Consequently, even when the acoustic transfer characteristic in the duct 21 varies as the result of variations in the temperature and the air flow speed depending upon the control state of the air conditioning system, the operational factor of the FIR filter 26 is changed by the adaptive filter 33 so that the amount of attenuated noise is prevented from being reduced according to the variations in the characteristic in the duct 21. Thus, the FIR filter 26** is controlled so that the amount of attenuated noise is usually rendered maximum. B. Operation of identification processing by the identification processing section:

The operation of identification of the transfer characteristic will now be described. The identification processing operation is performed prior to the above-described active noise attenuation control operation when the device is connected to a power supply. The terminals B of the respective change-over switches **29*a*, 29*b* are closed when the device is connected to the power supply. The M-sequence pseudorandom noise signal generated by the signal generator 38 as the identifying signal is supplied via the change-over switch 29*a* to the D/A converter 30, which converts the supplied signal to an analog signal. The analog signal is supplied to LPF 31, which cuts off the higher harmonics contained in the analog signal. Consequently, LPF 31 generates a signal containing only the components ranging in the frequency band of the noise to be attenuated. The signal generated by LPF 31 is supplied via the amplifier 32 to the loud speaker 23, whereupon it produces the identifying sound. The pseudorandom noise signal is also supplied to the synchronous adding circuit 39. The synchronous adding circuit 39 adds the supplied pseudorandom noise signals in synchronism with the signal periods and averages the signals. Since the pseudorandom noise signal is supplied directly from the signal generator 38 to the synchronous adding circuit 39, the signal supplied thereto contains no external noise. Consequently, the synchronous adding circuit 39 delivers the same signal as the supplied pseudorandom noise signal. On the other hand, the signal generated by the monitoring microphone 24 is supplied to the identifying adaptive filter 40 via the synchronous adding circuit 41. Accordingly, the signal input via the synchronous adding circuit 41 to the identifying adaptive filter 40 corresponds to the acoustic transfer characteristic of the transfer path including the synchronous adding circuit 41. The synchronous adding circuit 39 is provided for canceling the characteristic shift due to provision of the synchronous adding circuit 41 in the identifying adaptive filter 40** so that the identification is performed in the same condition.

The identifying sound produced from the loud speaker 23 propagates along the duct 21 and received by the monitoring microphone 24. The detection signal generated by the monitoring microphone 24 is supplied via BPF 35 to the A/D converter 36, which converts the detection signal to a digital signal. The digital signal is supplied to the synchronous adding circuit 41 via the change-over switch **29*b*. The synchronous adding circuit 41 adds the input signals in synchronism with the periods of the pseudorandom noise signals over 100 periods, for example, and averages the input signals. Consequently, the noise component other than the detection signal corresponding to the pseudorandom noise signal is damped by 20 dB so that the S/N ratio of the detection signal is improved. The detection signal generated by the synchronous adding circuit 41 is supplied to a reference input of the operation unit 42. The operation unit 42 obtains the difference between the input signal from the synchronous adding circuit 41 and the output signal from the identifying adaptive filter 40, thereby obtaining a resultant error value. The error value is supplied to the identifying adaptive filter 40. Upon receipt of the error value, the identifying adaptive filter 40 renews its factor so that its output corresponds to the reference signal. The LMS algorithm is employed for the renewal of the factor of the identifying adaptive filter 40. Upon completion of identification of the acoustic transfer characteristic $G_{AO}$, the digital filter 34 is set at the identified transfer characteristic $G_{AO}$ as its filter characteristic. Thereafter, the terminals A of the respective change-over switches 29***a*, 29*b* are closed, whereupon the above-described active noise attenuation control is performed by the control circuit 25.

The synchronous adding and averaging operation of each of the synchronous adding circuits 39 and 41 will now be described. Since the pseudorandom noise signal is a digital signal having the unit length of "511," as described above, the signal data periodically takes the same value every time the data is sampled 511 times. Noise and other signals are superimposed on the detection signals of the monitoring microphone 24 indicative of the detected pseudorandom noise signals. Accordingly, the digital signals supplied to the synchronous adding circuit 41 take random values. In each of the synchronous adding circuits 39, 41, the input signal data is averaged every time the data is sampled 511 times, so that the noise is reduced and the data of the component corresponding to the period of the digital signal is taken out. More specifically, since the digital signal input to each of the synchronous adding circuits 39, 41 has the period of 511, an average value of 511 data is obtained by operation. Each of the synchronous adding circuits 39, 41 has 511 built-in averaging units 44 connected in parallel with one another. Input and output terminals of each synchronous adding circuit are connected by the change-over switches 45*a*, 45*b* to one averaging unit 44 when the signal is in the same phase. In each averaging unit 44, the presently input data and the previously input data are averaged and an average value is delivered. In the embodiment, the average value of 100 sampled data is obtained for the purpose of obtaining the noise reduction by 20 dB. In this case, the input data is multiplied by 0.01 by the multiplier 46 of each averaging unit 44 so that the data value is reduced to 1/100. The data value reduced to 1/100 is added by an adder 47 to the data of the hitherto obtained average value and then, the average value data is stored in the register memory 48 and delivered at the output terminal $A_{out}$. Since one hundred data are averaged, the contact a of the change-over switch 49 is maintained in the closed state during the period from the initiation of processing of the synchronous addition to the one hundredth period, so that the data as it is stored in the register memory 48 is input to the adder 47. Upon input of a hundred and first data, the output of the register memory 48 is the data of an average value of one hundred data. The contact b of the change-over switch 49 is then closed so that the data of the register memory 48 is multiplied by 0.99 by the multiplier 50. The resultant data is supplied to the adder 47. Subsequently, each of the synchronous adding circuits 39, 41 delivers the detection signal whose level is equal to that of the average value of the data in one hundred periods. The switching operation of the change-over switch 49 as described above prevents divergence of the one hundred and first and subsequent data when each data is input. Furthermore, as the result of the above-described signal processing, the level of the output signal of each synchronous adding circuit is lower than the normal level in the first to ninety-ninth period. However, the output signal in the one hundredth period reaches its normal level. The output signals in the one hundred and first and subsequent periods are usually held at the normal level which is the same level as that of the input signals. When the synchronous addition and averaging are executed by each of the synchronous adding circuits 39, 41 in the manner as described above, the levels of the output signals resulting from addition of the data and averaging until the initial ninety-nine periods (99×511=50589 samples) are lower than those of the input signals. The level of the output signal is raised toward the normal level as the period is repeated. The output signals in the one hundredth and subsequent periods are at the normal level, and the level of the external noise relative to the M-sequence pseudorandom signal, that is, the S/N ratio can be improved. In this case, damping of prescribed 20 dB can be achieved in the one hundred and subsequent periods, whereby a sufficiently accurate detection signal is obtained. For the foregoing reason, the active noise attenuation control is executed after lapse of the time corresponding to one hundred periods or more for the identifying process.

Figure 4:
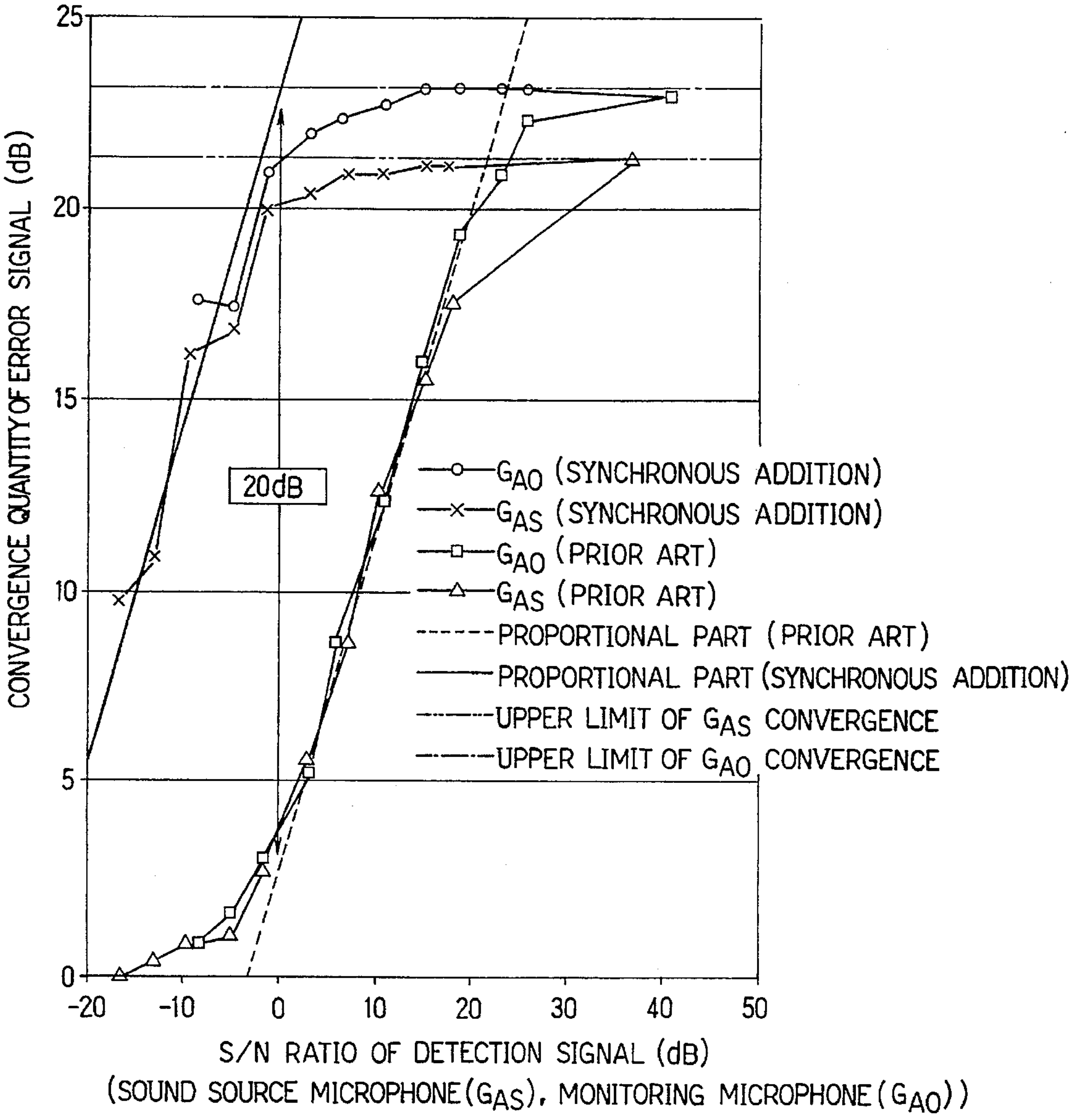
FIG. 4 is a graph showing the relationship between S/N ratios of detection signals and convergence of an error signal.

FIG. 4 shows the measurement results in the case where the synchronous adding and averaging operation is performed in one hundred periods and in the case where the synchronous adding and averaging operation is not performed. In each case, the identifying adaptive filter 40 employing the LMS algorithm is used in the identifying process. A convergence quantity of an error signal is employed as an index representative of the effect of the identifying process. The convergence quantity of the error signal indicates the degree of convergence of the identifying adaptive filter 40. In the embodiment, since the synchronous adding and averaging operation is performed in one hundred periods, the S/N ratio can be expected to be improved by 20 dB or the noise level can be expected to be reduced by 20 dB. In the measurement, the relationship between the S/N ratio of the detection signal of the monitoring microphone 24 and the convergence quantity of the error signal is obtained in the condition that the identifying sound produced from the loud speaker 23 according to the M-sequence pseudorandom noise signal is maintained at a predetermined level and further in the condition that the level of the noise propagating along the duct 21 is varied. Generally, the convergence quantity of the error signal has approximately the same upper limit value regardless of execution and non-execution of the synchronous adding and averaging operation. More specifically, the upper limit value of the convergence quantity of the error signal has some relation to linearity of the acoustic transfer characteristic of the transfer path of the signal to be identified or of the duct 21. The upper limit value tends to be larger as the acoustic transfer characteristic becomes linear. For example, the acoustic transfer characteristic $G_{AO}$ of the transfer path including that between the loud speaker 23 and monitoring microphone 24 has an upper limit value of the error signal larger than the acoustic transfer characteristic $G_{AS}$ of the transfer path including that between the loud speaker 23 and sound source microphone 22. The sound propagating along the duct 21 causes an inner duct wall surface to vibrate, and nonlinear sound component is produced by the vibration. Since the monitoring microphone 24 is disposed nearer to the loud speaker 23 than the sound source microphone 22, an amount of the non-linear sound component is smaller in the transfer path between the loud speaker 23 and the monitoring microphone 24 than in the transfer path between the loud speaker 23 and the sound source microphone 22 and accordingly, the lowering of linearity of the detected sound is small.

Upon drop of the S/N ratio of the detection signal of the sound source microphone 22 or the monitoring microphone 23, the lowering of the convergence quantity of the error signal becomes large in the case where the synchronous adding and averaging operation is not performed. Since the identifying adaptive filter 40 is adapted to a signal having an input-output interrelation, the identifying adaptive filter 40 converges by 3 or 4 dB even when the S/N ratio of the detection signal becomes zero. On the other hand, in the case where the synchronous adding and averaging operation is performed as in the embodiment, the noise component other than the detection signal from the monitoring microphone 24 or the sound source microphone 22 can be damped by 20 dB. Accordingly, the convergence quantity can be improved by 20 dB with respect to the same S/N ratio in the embodiment as compared with the case where the synchronous adding and averaging operation is not performed. Consequently, even in the condition that the level of the identifying signal is lower by 10 dB than that of the other noise component, for example, the convergence quantity of the error signal amounts to 10 dB or more when the synchronous adding and averaging operation is performed. In this case, even if the noise is propagating around, the identifying process can be performed when the identifying sound whose level is 10 dB lower than the noise level.

The switches 43*a*, 43*b* are provided for performing the identifying process in parallel with the active noise attenuating operation when the acoustic transfer characteristic $G_{AO}$ has varied during the active noise attenuating operation. Each of the switches 43*a*, 43*b* is turned on only when the identifying process is performed during the noise attenuating operation. The identifying process is performed by the identification control section 37 in the manner as described above when the switches 43*a*, 43*b* are turned on. The acoustic transfer characteristic can be identified as the result of the synchronous adding and averaging process of the M-sequence pseudorandom noise signals in 100 periods even when the S/N ratio of the detection signal from the monitoring microphone 24 is approximately 10 dB lower than the noise, for example. Accordingly, the identifying process can be performed with the pseudorandom noise signal whose level is lower than that of the noise propagating along the duct 21, without interfering the active noise attenuating operation. Consequently, even when the acoustic transfer characteristic in the duct 21 has varied, the identification of the acoustic transfer characteristic $G_{AO}$ can be accurately performed such that the noise attenuating effect can be maintained at its maximum. When the switches 43*a*, 43*b* has been turned on, the identifying process can be performed no matter which of the terminals A and B of the respective change-over switches 29*a*, 29*b* is closed. Furthermore, the renewal of the factor of the FIR filter 26 by the adaptive filter 33 is interrupted when the identification process is performed in parallel with the noise attenuating operation. There is a possibility that the M-sequence pseudorandom noise signal detected by the monitoring microphone 24 may become noise for the noise attenuation signal and that the adaptive control operation may be disturbed.

According to the above-described embodiment, the M-sequence pseudorandom noise signal serving as the identification signal is generated by the signal generator 38 to be delivered to the loud speaker 23, which produces the identification sound into the duct 21. The identification sound is received by the monitoring microphone 24, which delivers the detection signal to the synchronous adding circuit 41. In the synchronous adding circuit 41, the input detection signals are added and averaged in 100 periods in synchronism with the period of the identification signal, whereby the acoustic transfer characteristic $G_{AO}$ is identified. Consequently, the S/N ratio of the detection signal can be improved by 20 dB and the identification process with high accuracy can be performed such that the amount of noise attenuated by the active noise attenuation control can be maintained at its maximum.

Furthermore, the identification process can be reliably performed even when the level of the identification signal indicative of the identification sound produced from the loud speaker 23 is low. Consequently, since the identification process can be performed even while the conditioned air from the air conditioning system or the noise is propagating in the duct 21, the air conditioning operation can be promptly started up.

Additionally, even when the change in the control state by the air conditioner varies the acoustic transfer characteristic in the duct 21 while the active noise attenuation control is being performed during the air conditioning control, the active noise attenuation control can be performed with the varying acoustic transfer characteristic being identified. Consequently, since operation of the air conditioning system need not be interrupted every time the acoustic transfer characteristic in the duct 21 varies, the air conditioning efficiency can be prevented from being lowered.

Figure 5:
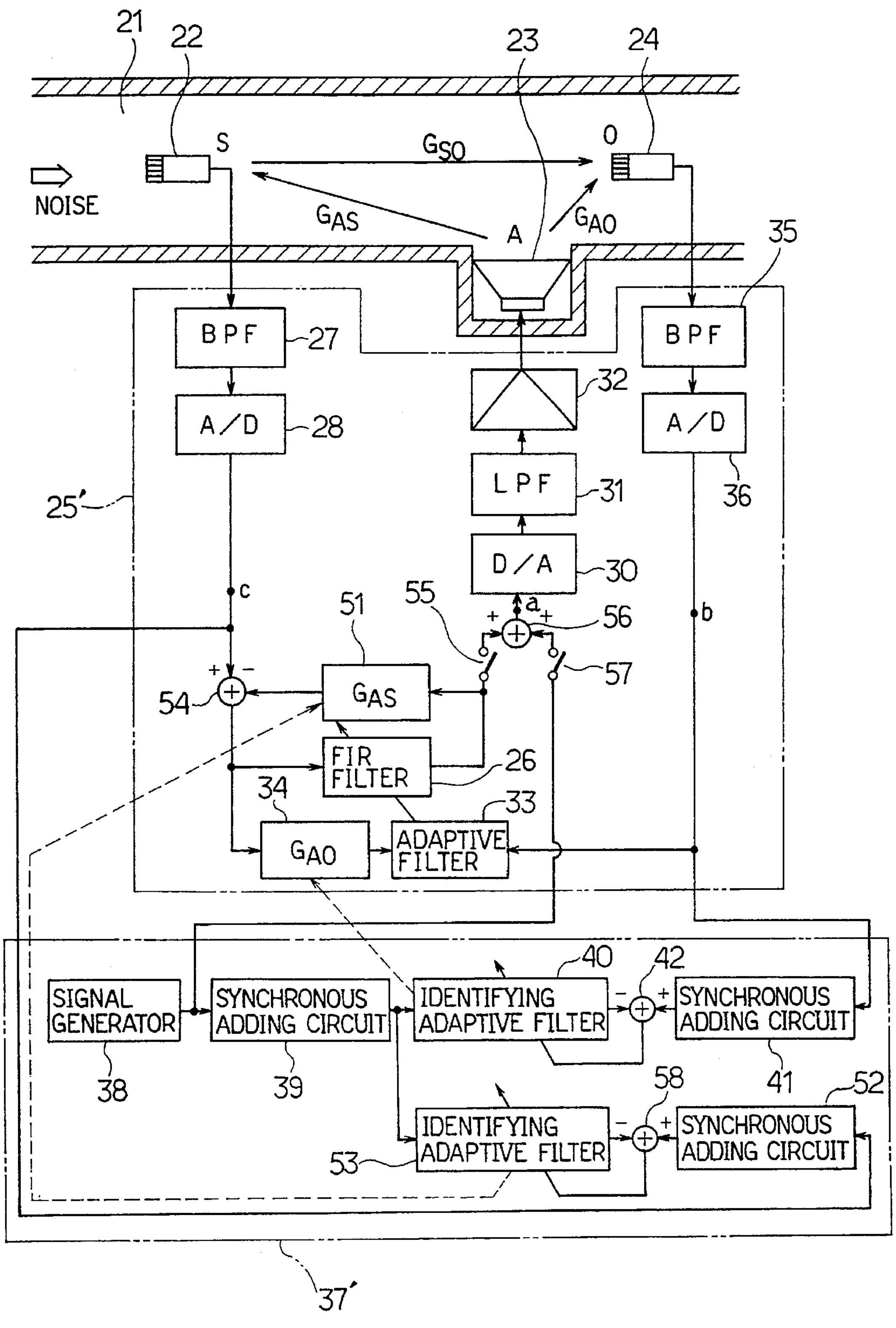
FIG. 5 is a view similar to FIG. 1 showing a second embodiment of the active noise attenuating device in accordance with the present invention.

FIG. 5 illustrates a second embodiment of the present invention. In the second embodiment, the control circuit 25' is provided with a digital filter 51 having an acoustic transfer characteristic $G_{AS}$ in order that the sound produced from the loud speaker 23 can be prevented from being detected by the sound source microphone 22. Furthermore, the identification control section 37' is provided with a synchronous adding circuit 52 and an identifying adaptive filter 53 so that the acoustic transfer characteristic of the digital filter 51 is identified by the synchronous adding and averaging process.

In FIG. 5, the A/D converter 28 is connected to the FIR filter 26 and the digital filter 34 via an operation unit 54. An output signal of the digital filter 51 set at the filter characteristic $G_{AS}$ is supplied to the operation unit 54 as subtraction input. An output signal of the FIR filter 26 is supplied to the digital filter 51 and the D/A converter 30 via a switch 55 and an adder 56. The output signal of the signal generator 38 is supplied to the D/A converter 30 via a switch 57 and the adder 56. The detection signal from the A/D converter 28 is supplied to the synchronous adding circuit 52 and also to an operation unit 58 as a reference signal. An output signal of the identifying adaptive filter 53 is also supplied to the operation unit 58. The operation unit 58 obtains the difference between the output signal from the filter 53 and the reference signal, which difference serves as the error signal. The identifying adaptive filter 53 identifies the acoustic transfer characteristic $G_{AS}$ of the transfer path between point "a" at the input side of the D/A converter 30 and point "c" at the output side of A/D converter 28 via LPF 31, the amplifier 32, the loud speaker 23, the duct 21, the sound source microphone 22 and BPF 27 in turn. The digital filter 51 is set to the acoustic transfer characteristic $G_{AS}$ identified by the filter 53 as its filter characteristic.

The control sound produced from the loud speaker 23 propagates to the side of the sound source microphone 22 in the duct 23. If the control sound is received by the sound source microphone 22, it generates a detection signal indicated of the received control sound. Another control sound is produced from the loud speaker 23 for attenuating the received control sound. In this case, a so-called howling may occur. The howling is likely to occur particularly when the distance between the sound source microphone 22 and the loud speaker 23 is short or when a non-directional microphone is employed as the sound source microphone 22. In view of the above-described problem, the control signal generated by the FIR filter 26 is supplied to the digital filter 51 as well as to the loud speaker 23. The operation unit 54 is provided for subtracting, from the detection signal indicative of the noise received by the microphone 22, the component of the sound produced from the loud speaker 23 to be received by the microphone 22. In this regard, the digital filter 51 is set for the filter characteristic corresponding to the acoustic transfer characteristic $G_{AS}$ of the transfer path between points "a" and "c" in the transfer path of the control circuit 25'. Accordingly, output of the digital filter 51 can be equaled to the component of the sound produced from the loud speaker 23 to be received by the sound source microphone 22. Consequently, the operation unit 54 is designed to perform an operation so that the component of the sound produced from the loud speaker 23 to be received by the sound source microphone 22 is canceled to be prevented from being contained in the input signal to the FIR filter 26.

The identification process of the acoustic transfer characteristic GAS will now be described. The switch 55 is turned off and the switch 57 is turned on. The M-sequence pseudorandom noise signal is generated by the signal generator 38 in the same manner as in the identification of the acoustic transfer characteristic $G_{AO}$. The detection signal indicative of the sound received by the sound source microphone 22 is supplied via the A/D converter 28 to the synchronous adding circuit 52, which processes the detection signal. The acoustic transfer characteristic $G_{AS}$ is identified by the identifying adaptive filter 53. The filter characteristic of the digital filter 51 is set on the basis of the identified characteristic $G_{AS}$. Upon setting of the filter characteristic $G_{AS}$ of the digital filter 51, the switch 57 is turned off and the switch 55 is turned on, so that the active noise attenuation control operation is performed by the control circuit 25'. Furthermore, when the acoustic transfer characteristic $G_{AS}$ is identified during the active noise attenuation control operation, both switches 55 and 57 are turned on. Since the M-sequence pseudorandom signal form the signal generator 38 is supplied to the D/A converter 30 via the adder 56, it is not supplied to the side of the digital filter 51. The renewal of the factor of the FIR filter 26 by the adaptive filter 33 is interrupted during the identification process such that the factor is fixed. Consequently, the active noise control is not influenced even when the low level M-sequence pseudorandom noise signal is generated.

According to the second embodiment, the same effect can be achieved as in the first embodiment. Furthermore, variations in the flow speed of the conditioned air from the air conditioning system and in the temperature vary the acoustic transfer characteristics $G_{AS}$ and $G_{AO}$. The variation in the characteristic $G_{AS}$ is larger than in the characteristic $G_{AO}$ when the distance of the transfer path between the loud speaker 23 and the sound source microphone 22 is longer than that of the transfer path between the loud speaker 23 and the monitoring microphone 24. Even in such a case, the acoustic transfer characteristic $G_{AS}$ can be identified so that the active noise attenuation control can be performed. Consequently, only the noise can be detected and the amount of attenuated noise can be rendered maximum.

Figure 6:
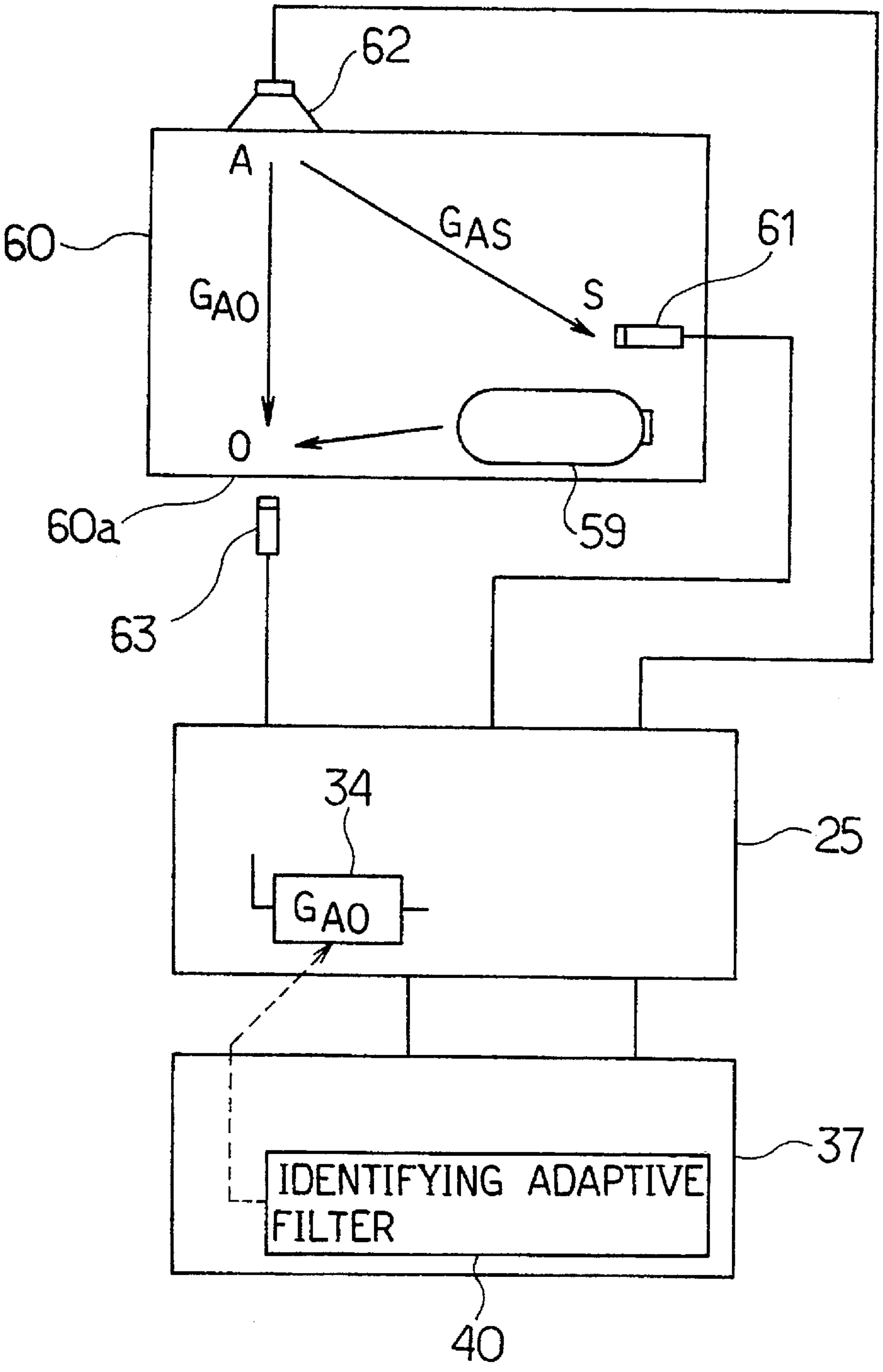
FIG. 6 is a view similar to FIG. 1 showing a third embodiment of the active noise attenuating device in accordance with the present invention.
Figure 7:
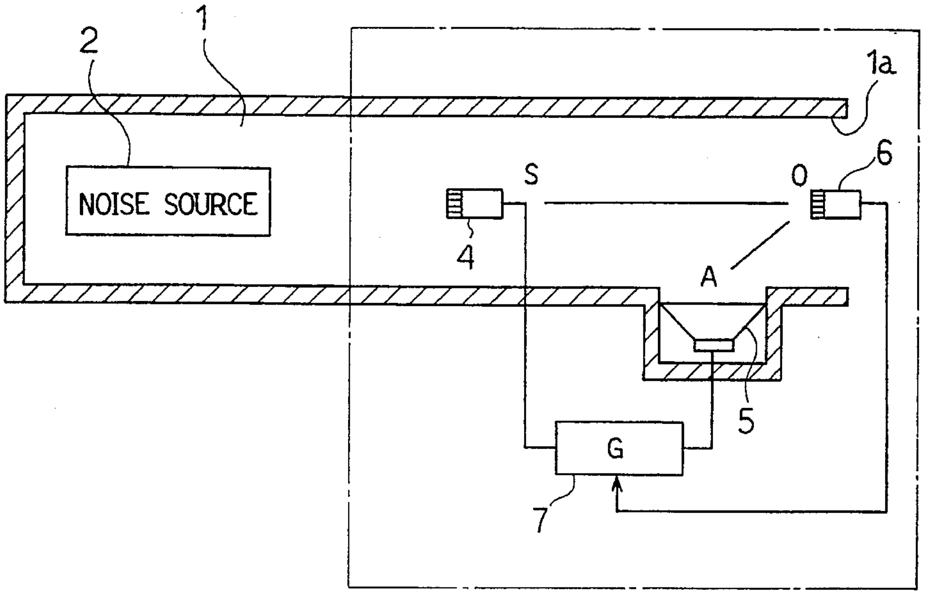
FIG.7 PRIOR ART
FIG. 7 is a view similar to FIG. 1 showing a prior art active noise attenuating device.
Figure 8:
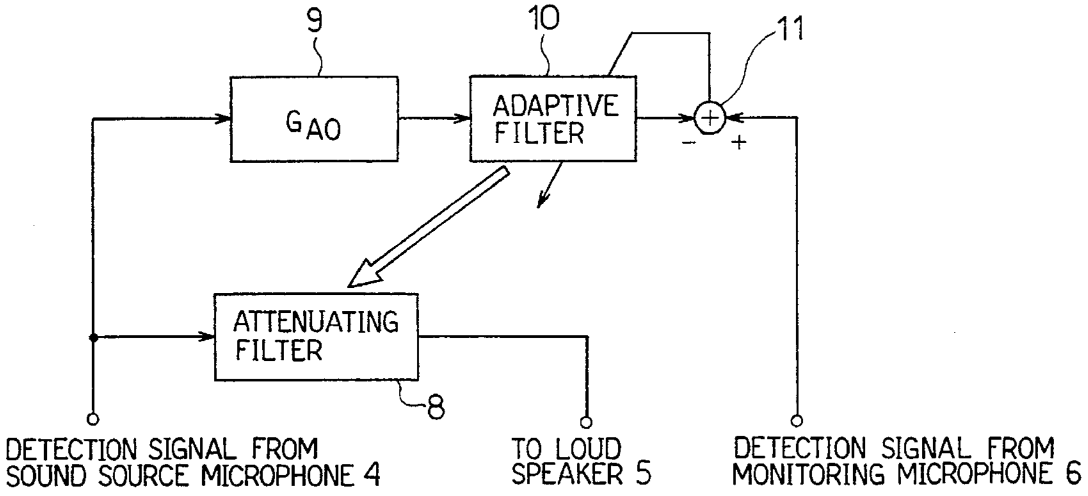
FIG.8 PRIOR ART
FIG. 8 is a schematic block diagram showing a prior art adaptive control.

FIG. 6 illustrates a third embodiment of the invention. In the embodiment, the active noise attenuating device is provided in a refrigerator for attenuating noise produced by a compressor composing a refrigeration cycle of a refrigerating unit.

In FIG. 6, a compressor 59 serving as the noise source is disposed in a duct 60 of a component chamber serving as the propagation path of the noise. The duct 60 has a radiating opening 60*a* formed therein to be away from the compressor 59. The noise produced from the compressor 59 being driven propagates outward through the radiating opening 60*a*. The noise from the compressor 59 is received by the sound source microphone 61 serving as sound receiving means, which generates the detection signal. The control sound is generated on the basis of the detection signal and is produced from the loud speaker 62 serving as a control sound producer so that the sound interference is caused in the opening 60*a*. The monitoring microphone 63 serving as a second sound receiving means is provided in the vicinity of the opening 60*a*. The control circuit 25 performs the adaptive control so that the amount of attenuated noise is rendered maximum at point O.

According to the third embodiment, the acoustic transfer characteristic can be identified while the noise is being produced from the compressor. The compressor 59 can be driven regardless of the identification process simultaneously when the refrigerator is connected to the power supply. Consequently, the refrigerating unit can be started up promptly.

Although the M-sequence pseudorandom noise signal is employed as the identification signal in the foregoing embodiments, another random noise signal having different periodicity may be employed. Furthermore, a sine wave having the frequency ranged in the frequency band of the noise to be attenuated may be produced at intervals of 0.1 Hz to be synthesized into a signal. Additionally, an impulse signal may be employed as the identification signal.

Although the M-sequence pseudorandom noise signal has the unit length of "511" in the foregoing embodiments, the signal having another unit length may be employed depending upon the accuracy of the detection signal.

Although the sound source microphone 61 is employed as the first sound receiving means detecting the noise from the compressor 59 in the third embodiment, a vibration pick-up sensor detecting vibratory sound of the compressor 59 may be employed as the first sound receiving means.

The foregoing description and drawings are merely illustrative of the principles of the present invention and are not to be construed in a limiting sense. Various changes and modifications will become apparent to those of ordinary skill in the art. All such changes and modifications are seen to fall within the true spirit and scope of the invention as defined by the appended claims.

We claim:

1. An adaptive control type active noise attenuating device, comprising:

a first microphone provided in a propagation path of noise for receiving the noise and generating a detection signal indicative thereof;

a loud speaker provided downstream from the first microphone along the noise propagation path;

a second microphone provided downstream from the loudspeaker along the noise propagation path for receiving sound and generating a detection signal indicative thereof;

operation means for executing an operation on the basis of the detection signal from the first microphone to generate a control signal supplied to the loudspeaker to produce a sound interfering with the noise, whereby the noise is attenuated;

adaptive control means, connected to receive detection signals from the first and second microphones, for adjusting an operational factor of the operation means on the basis of the detection signals supplied thereto from the first and second microphones respectively so that an amount of noise attenuated by the sound produced by the loudspeaker is at a maximum;

a filter means coupled between the first microphone and the adaptive control means for filtering the signal from the first microphone according to a predetermined transfer characteristic;

a signal generator delivering to the loudspeaker an identifying signal generated so as to be repeated in predetermined periods and having frequency components ranging in a frequency band of the noise to be attenuated;

first synchronous adding means for adding the detection signals generated by the second microphone synchronously with the period of the identifying signal produced by the signal generator in a plurality of periods, wherein the detection signals are generated by the second microphone when the sound representing the identifying signal produced by the loudspeaker is received by the second microphone, and wherein the first synchronous adding means obtains an average value of the added detection signals and generates an output signal indicative of the obtained average value; and adaptive control identification control means for identifying a transfer characteristic of a transfer path between the loudspeaker and the second microphone on the basis of the output signal from the first synchronous adding means and the identifying signal and for adjusting the filtering characteristic of the filter means so that the filtering characteristic is identical to the identified transfer characteristic.

2. An active noise attenuating device according to claim 1, wherein the adaptive control identification control means has an input section to which the identifying signal is supplied and comprises:

first adding means provided in the input section of the adaptive control identification control means for adding the identifying signals supplied thereto from the signal generator in the plurality of periods synchronous with the periods of the identifying signals, wherein the first adding means obtains the average value of the added identifying signals.

3. An active noise attenuating, device according to claim 1, wherein the signal generator generates M-sequence pseudorandom noise having a predetermined duration and repeated in predetermined periods as the identifying signal.

4. An active noise attenuating device according to claim 1, wherein the first synchronous adding means comprises:

a plurality of averaging units to which a predetermined number of signals are input wherein the input signals are obtained by utilizing a switching means to sequentially switch among the averaging units to be connected to the signal generator synchronous with the period of the identifying signal to supply one period of the identifying signal to each of the averaging units, each averaging unit adding the input signals from periods of the identifying signal and obtaining the average value of the added input signals.

5. An active noise attenuating device according to claim 4, wherein each averaging unit comprises:

operation means for sequentially adding the input signals and sequentially obtaining the average value of the input signals until the predetermined number of input signals in the predetermined period is reached; and storage means for sequentially storing the average values of the input signals wherein thereafter, the operation means adds the input signal weighted with a value corresponding to a first adding operation to the average value and obtains a new average value, which is stored in the storage means.

6. An active noise attenuating device according to claim 1, further comprising:

cancel means provided with a transfer characteristic identical to that of a transfer path between the loudspeaker and the first microphone for subtracting a cancel signal from the detection signal generated by the first microphone, the cancel signal being obtained by filtering the control signal generated by the operation means;

second synchronous adding means for adding the detection signals generated by the first microphone synchronously with the period of the identifying signal in a number of periods, said detection signals being generated by the first microphone when the sound produced by the loudspeaker representing the identifying signal is received by the first microphone, the second synchronous adding means obtaining an average value of the added detection signals and generating an output signal indicative of the obtained average value; and canceling identification control means for identifying a transfer characteristic of a transfer path between the loudspeaker and the first microphone on the basis of the output signal of the second synchronous adding means and the identifying signal and for adjusting the transfer characteristic of the cancel means on the basis of the identified transfer characteristic.

7. An active noise attenuating device according to claim 6, wherein the second synchronous adding means comprises a plurality of averaging units to which a predetermined number of signals are input wherein the input signals are obtained by utilizing a switching means to sequentially switch among the averaging units to be connected to the signal generator synchronous with the periods of the identifying signal, each averaging unit adding the input signals from periods of the identifying signal and obtaining the average value of the added input signals.

8. An active noise attenuating device according to claim 6, wherein the cancelling identification control means has an input section to which the identifying signal is supplied and comprises a second adding means provided in the input section of the cancelling identification control means for adding the identifying signals supplied by the signal generator in the plurality of periods synchronous with the periods of the identifying signal, the second adding means obtaining an average value of the added identifying signal.

9. An active noise attenuating device according to claim 8, wherein the second adding means comprises a plurality of averaging units to which a predetermined number of signals are input wherein the input signals are obtained by utilizing a switching means to sequentially switch among the averaging units to be connected to the signal generator synchronous with the periods of the identifying signals to supply one period of the identifying signal produced by the signal generator to each of the averaging units, each averaging unit adding the input signals in the periods of the identifying signal and obtaining the average value of the added input signal.

* * * * *